United States Patent
Pedrazzini

(10) Patent No.: US 8,795,144 B2
(45) Date of Patent: Aug. 5, 2014

(54) CENTRIFUGATION APPARATUS FOR CONTAINERS OF BIOLOGICAL MATERIAL INCLUDING CONVEYOR, TURNTABLE AND CENTRIFUGES

(75) Inventor: Gianandrea Pedrazzini, Paradiso (CH)

(73) Assignee: Inpeco Holding Ltd., Valletta (MT)

( * ) Notice: Subject to any disclaimer, the term of this patent is extended or adjusted under 35 U.S.C. 154(b) by 1028 days.

(21) Appl. No.: 12/867,345

(22) PCT Filed: Feb. 11, 2009

(86) PCT No.: PCT/IB2009/050562
§ 371 (c)(1),
(2), (4) Date: Aug. 12, 2010

(87) PCT Pub. No.: WO2009/101587
PCT Pub. Date: Aug. 20, 2009

(65) Prior Publication Data
US 2011/0045958 A1  Feb. 24, 2011

(30) Foreign Application Priority Data
Feb. 13, 2008 (IT) .............................. MI2008A0228

(51) Int. Cl.
*B04B 5/10* (2006.01)
(52) U.S. Cl.
USPC .............................................. 494/20; 494/31
(58) Field of Classification Search
USPC ................................ 494/16, 31, 33, 20; 422/72
See application file for complete search history.

(56) References Cited

U.S. PATENT DOCUMENTS

| | | | |
|---|---|---|---|
| 3,240,425 A * | 3/1966 | Ray et al. | 494/10 |
| 6,586,255 B1 * | 7/2003 | Hubert et al. | 436/45 |
| 6,589,789 B1 * | 7/2003 | Hubert et al. | 436/45 |
| 6,872,360 B1 | 3/2005 | Cohen et al. | |
| 6,945,129 B2 * | 9/2005 | Escal | 73/864.24 |
| 7,112,303 B2 * | 9/2006 | Itoh | 422/72 |
| 7,115,090 B2 * | 10/2006 | Lagarde | 494/10 |

(Continued)

FOREIGN PATENT DOCUMENTS

| | | |
|---|---|---|
| DE | 200 15 684 U1 | 2/2001 |
| JP | 61-13158 A | 1/1986 |
| JP | 1-189359 A | 7/1989 |
| JP | 2000-84436 A | 3/2000 |

*Primary Examiner* — Charles E Cooley
(74) *Attorney, Agent, or Firm* — Birch, Stewart, Kolasch & Birch, LLP

(57) ABSTRACT

An apparatus for automatically centrifuging test tubes containing biological material including a plurality of centrifuges functionally identical to one another yet independent and adapted to centrifuge test tubes offered to an interface for centrifuging test tubes using a conveying system included in an automatic conveyor of test tubes. The plurality of centrifuges is fitted on a turntable adapted to offer each centrifuge at a suitable loading/unloading point adjacent to the loading/unloading point of the interface. Each centrifuge is provided with a motor adapted to generate the centrifugal motion by setting a rotor in rotation, and a test tube handling device including an arm with a first gripper adapted to load test tubes to be centrifuged and a second gripper adapted to unload centrifuged test tubes, simultaneously to the loading, the arm sliding along a curved guide adapted to generate a forced rotation of the grippers.

14 Claims, 10 Drawing Sheets

(56) References Cited

U.S. PATENT DOCUMENTS

| | | | |
|---|---|---|---|
| 7,195,737 B2* | 3/2007 | Itoh | 422/72 |
| 7,963,900 B2* | 6/2011 | Miller | 494/37 |
| 2004/0184959 A1* | 9/2004 | Itoh | 422/72 |
| 2006/0116269 A1* | 6/2006 | Lagarde | 494/1 |
| 2007/0059209 A1* | 3/2007 | Pang et al. | 422/72 |
| 2009/0047179 A1* | 2/2009 | Ping et al. | 422/72 |
| 2011/0045958 A1* | 2/2011 | Pedrazzini | 494/8 |
| 2014/0045670 A1* | 2/2014 | Smith et al. | 494/37 |

\* cited by examiner

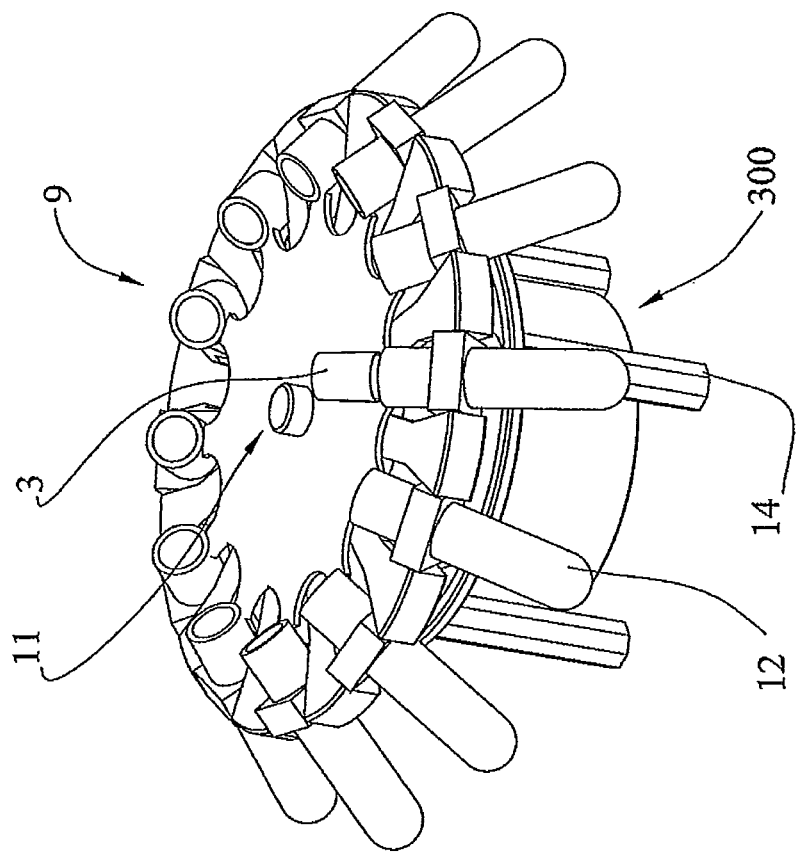
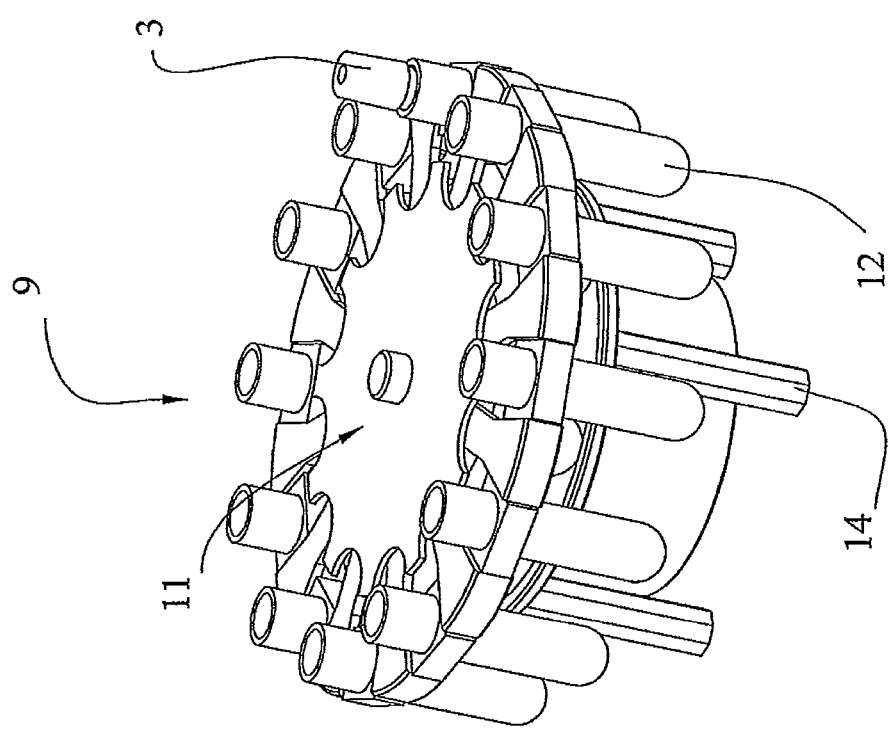
FIG.3
FIG.4

CENTRIFUGATION APPARATUS FOR CONTAINERS OF BIOLOGICAL MATERIAL INCLUDING CONVEYOR, TURNTABLE AND CENTRIFUGES

BACKGROUND OF THE INVENTION

1. Field of the Invention

The present invention relates to an apparatus for centrifuging biological material containers, or test tubes, in a context of laboratory automation.

2. Description of the Related Art

The scientific progress and the development in technology produced a major development in Laboratory Medicine with a subsequent growth of the requested analyses, both in typology and number.

The efficiency of a laboratory is evaluated by calculating the TAT (Turn Around Time), i.e. the time elapsing between the moment in which a test tube, once identified, starts the processing process and the moment in which the results of the required analyses on such a test tube are obtained. The lower the TAT, the higher the efficiency of a laboratory.

With the introduction of automation, the Laboratory Medicine has faced the increase in required analyses while succeeding in accelerating the application times of the analyses (reduction of TAT) and improving the analytical quality thereof, due to the features of better precision and accuracy of the automated processes.

Automation means both the use of devices adapted to automate single processing steps and analysis of the biological material samples, and the use of conveyors adapted to automatically convey such samples to said automation devices possibly interfaced to the conveyor. The automation development also involved the step of centrifuging the biological material samples, thus introducing devices adapted to simultaneously centrifuge a multitude of test tubes, such as for example centrifuges capable of processing batches of 80 or more test tubes at once, and which are therefore not suitable for managing the processing of single test tubes whose analysis are urgently required (in cases of patients undergoing surgery or similar emergencies inside hospital wards or emergency rooms), nor suitable for obtaining low TAT values for each single test tube as well.

The automation systems implemented and used heretofore only dealt with the automation of the traditional centrifuging cycle which was once manually operated, by replacing the human operator with operations performed by robot operators.

This setting has made a series of limits arise, which are inherent to the original process and thwarted the evolution towards concepts which are new and more suitable for an automatic process, while succeeding in overcoming the constraints of the manual process.

In actual fact, aiming to help the human operator in order to provide him/her with a limited and time-constrained burden of load/unload, the traditional process pushed towards the implementation of centrifuging machines of ever-increasing size and power.

But these machines do not provide for any optimisation of the time for processing a test tube because, due to the organisation of the loading/unloading process of the centrifuges, the test tubes being centrifuged in batches may remain even several minutes waiting in the centrifuge prior being loaded or unloaded.

JP-61-013158 discloses an apparatus with a plurality of centrifuges.

SUMMARY OF THE INVENTION

It is the object of the present invention to implement an apparatus adapted to centrifuge biological material containers, or test tubes, capable of shortening the processing times of a small number of test tubes as compared to normal load volumes of the presently marketed centrifuges, and integrated in a context of laboratory automation, so as to solve the aforementioned problems.

In accordance with the invention, the object is achieved by an apparatus for automatically centrifuging test tubes containing biological material including a plurality of centrifuges functionally identical to one another yet independent and adapted to centrifuge test tubes offered to an interface for centrifuging test tubes by means of a conveying system included in an automatic conveyor of test tubes, the plurality of centrifuges rotatably mounted on a turntable adapted to offer each centrifuge at a suitable loading/unloading point adjacent to the loading/unloading point of the interface, wherein each centrifuge is provided with a motor adapted to generate the centrifugal motion by setting a rotor in rotation, and a test tube handling device comprising an arm with a first gripper adapted to load test tubes to be centrifuged and a second gripper adapted to unload centrifuged test tubes, simultaneously to the loading, the arm sliding along a curved guide adapted to generate a forced rotation of the grippers.

The size of such centrifuges is smaller than those typically used in the laboratories for large routines. In this case, the centrifuges have no rotors fitting yokes intended to contain pluralities of test tubes, but have rotors accommodating single test tubes and holding the test tubes at 45° with respect to the vertical in the centrifuging step.

Such a feature allows a centrifuging process which is more effective and has a considerably shortened length than yoke-type centrifuges. Furthermore, there exist technologies for rotor construction not requiring the same to be balanced, thus allowing to load test tubes without any control over their position and weight.

It is a further advantage that both the size and shape of the rotor make the process much more reliable and not subject to hazards of explosion of the rotating equipment.

This is crucial to the new concept of automating the centrifugation, since it allows to renounce to the process conceived in "batches" to then be able to pass to a process having the features of a continuous process.

The described apparatus is specifically suitable for centrifuging test tubes conveyed on an automatic conveying system which need to be processed with priority with respect to other ones in the environment of an analysis laboratory. Such an apparatus is intended to the following object as it is equipped with several reciprocally independent centrifuges adapted to centrifuge small numbers of test tubes at once.

Furthermore, the reduction of the processing times in this type of centrifuging systems is not only obtained by decreasing the waiting times for loading/unloading the test tubes, but by the technology that forms such centrifuges allowing the rotor to self-balance during the centrifugation, thus avoiding the automation system from needing to provide balancing and weighting of the loaded test tubes.

The described apparatus object of the present invention, represents an optimal solution for managing test tubes to be centrifuged within an automation system for biological material samples capable of simultaneously processing high volumes of test tubes.

BRIEF DESCRIPTION OF THE DRAWINGS

These and other features of the present invention will be more apparent upon the following detailed description of its practical embodiments, illustrated by way of non-limitative example in the accompanying drawings, in which:

FIG. 3 shows a perspective view of a single centrifuge in a stop position;

FIG. 4 shows a perspective view of a single centrifuge during a centrifuging step;

DESCRIPTION OF THE PREFERRED EMBODIMENTS

Figure 1:
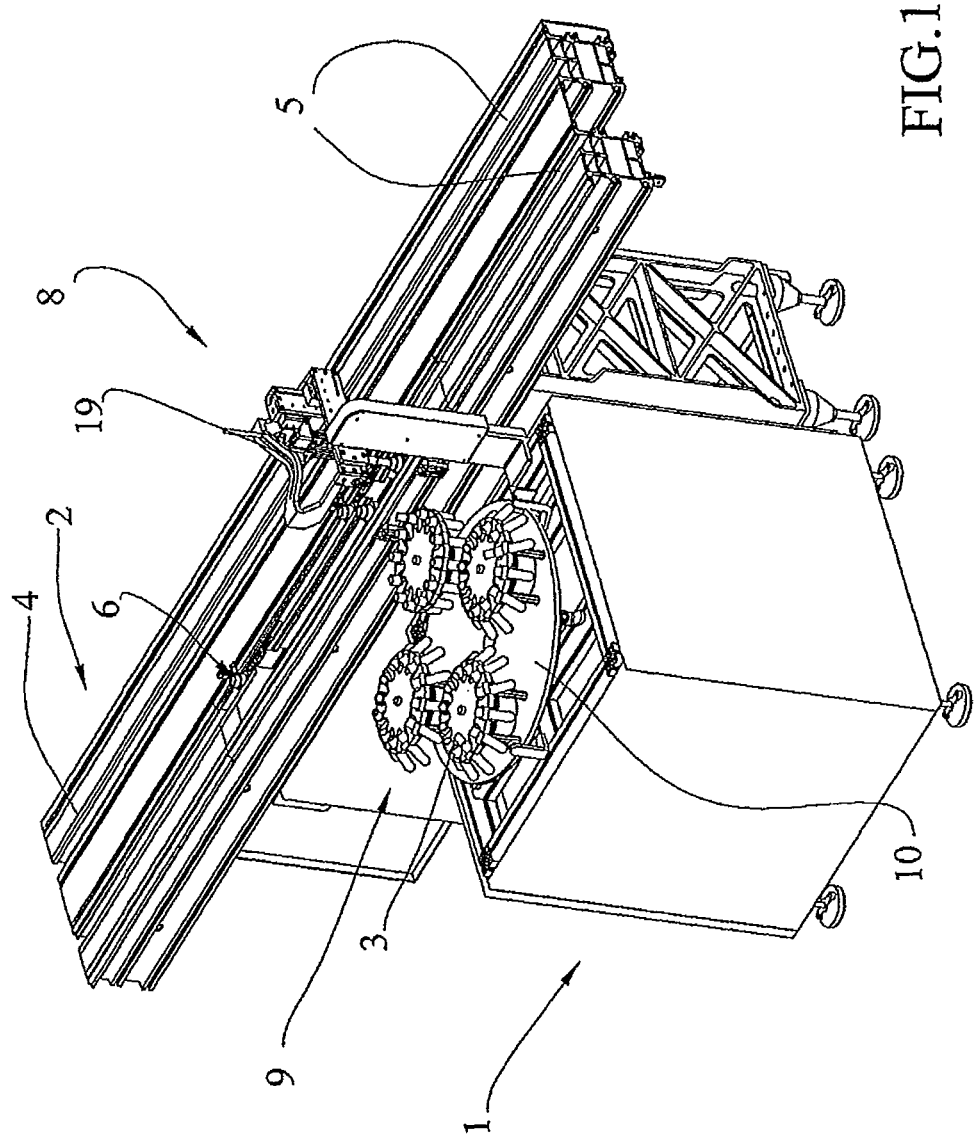
FIG. 1 shows a perspective view of the apparatus for centrifuging test tubes included in an automation system.

FIG. 1 depicts a centrifuging apparatus 1 connected to a conveyor 2 adapted to automatically convey test tubes 3 containing biological material samples.

Said conveyor 2 consists of a conveyor belt 4 responsible for the automatic conveying of test tubes 3 towards further modules for processing and analysing biological material samples. Such a conveyor belt 4 comprises primary and secondary lanes 5 playing the role of conveying test tubes towards the processing and analysing modules.

The aforementioned embodiment offers said conveyor 2 as an interface to the described centrifuging apparatus 1, but implementing other types of interfaces is however possible, as long as the test tubes are offered in a position suitable to be handled, as it will be later described.

Conveying the test tubes 3 on the conveyor belt 4 is allowed by the use of suitable test tube conveying devices 6 which ensure the verticality and stability of the test tubes being processed. Such conveying devices 6 are appropriately deviated and stopped on the conveyor belt by means of specific deviating and stopping devices included in the conveyor 2, as described in the Italian Patent Application MI2007A002254.

Figure 2:
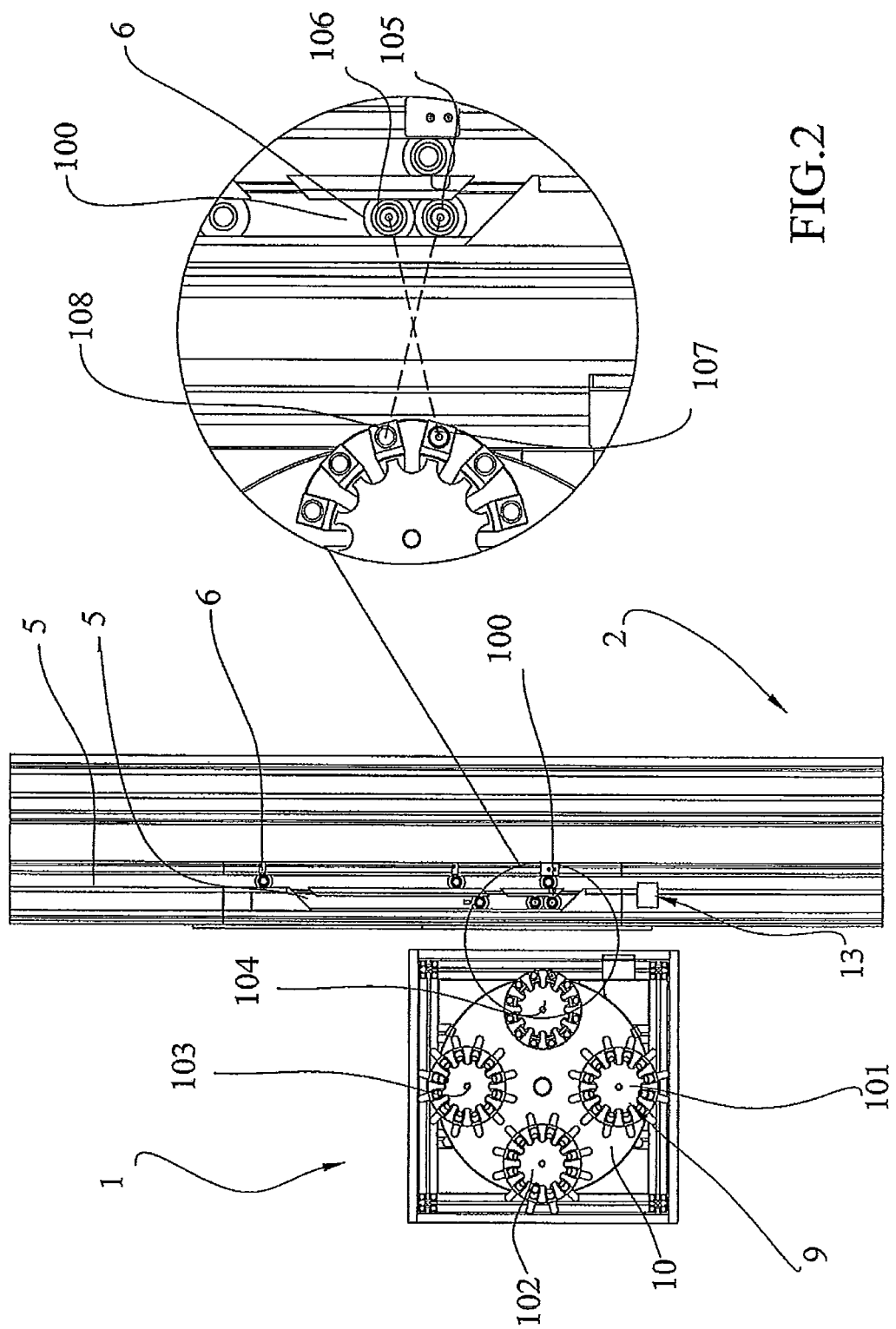
FIG. 2 shows a top plan view of the apparatus for centrifuging test tubes.

The test tubes 3 conveyed by the conveyor 2 needing to be centrifuged are conveyed in the lane 5 interfacing with the described apparatus and stopped at position 100, where they may be handled by a handling device 8 (FIGS. 1 and 2, in FIG. 2 such a handling device 8 has been removed in order to better point out position 100).

The centrifuging apparatus 1 (FIG. 2) includes a determined number of centrifuges 9 adapted to centrifuge a maximum number of twelve test tubes at each centrifuging cycle.

The number of centrifuges 9 may vary: the aforementioned embodiment comprises four centrifuges, independently operating from one other.

The centrifuges 9 are fastened to a turntable 10 adapted to offer the centrifuges in a position suitable for loading and unloading the test tubes by means of the handling device 8.

The operation of loading/unloading a centrifuge 9 is independent from the centrifuging cycle of the other three: these two operations may indeed be performed in parallel, thus allowing three centrifuges to operate at the three positions 101, 102 and 103 (FIG. 2), while the fourth centrifuge 9 at position 104 is unloaded from the newly centrifuged test tubes and loaded with test tubes to be centrifuged.

The technology offered by the already marketed centrifuges 9 includes a self-balancing mechanism such that the automation system does not need to provide for weighting and balancing procedures of the test tubes loaded in a centrifuge, which actions are instead performed in the current systems for centrifuging biological material samples. Such centrifuges 9 comprise rotors 11 (FIGS. 3 and 4) being therefore able to perform perfectly balanced centrifugations irrespective of the weight, distribution and number of test tubes which are loaded in the single centrifuge.

This feature has the apparent advantage of simplifying the whole automation system, thus considerably accelerating the process of loading the test tubes in the centrifuge.

A loaded centrifuge 9 may start the centrifugation, whose length and speed are determined according to the requirements from the analysis laboratory where the operation is carried out. The rotors 11 comprise twelve yokes 12 (FIGS. 3 and 4) intended to accommodate single test tubes 3 which keep a 45° tilt with respect to the vertical, in the centrifuging step.

The possibility of keeping the tilt of the yokes within 45° with respect to the vertical allows to obtain the same effects in a shorten centrifuging time, as it is demonstrated that the centrifugation with such a tilt is more effective.

FIG. 3 shows a single centrifuge 9 when the rotor 11 is stopped: as it may be seen, the yokes 12 are perfectly vertical as well as the test tubes 3 contained therein. FIG. 4 shows a centrifuge when the rotor is moving: the yokes 12 and the test tubes 3 contained therein are tilted by 45° with respect to the vertical.

Each centrifuge 9 is fastened to the turntable 10 by means of mounts 14 (FIGS. 3 and 4) and the centrifugal movement is generated by a motor 300 belonging to each centrifuge 9.

FIG. 1 depicts the apparatus 1 during the processing of three centrifuges and the process of loading/unloading one of them, at position 104. When a centrifuge 9 finishes its own centrifuging cycle, it is arranged at position 104 by rotating the turntable 10, so as to allow the process of loading/unloading such a centrifuge 9 by the test tube handling device 8, capable of reaching both the yokes 12 of the centrifuge at position 104, and the position 100 on the conveyor 2 (FIG. 2).

Close to position 100, the conveyor may comprise test tube identification devices 13 which identify the centrifuged and unloaded test tube, by reading its bar code included in the tag arranged on the side body of the test tube, for example.

Figure 5:
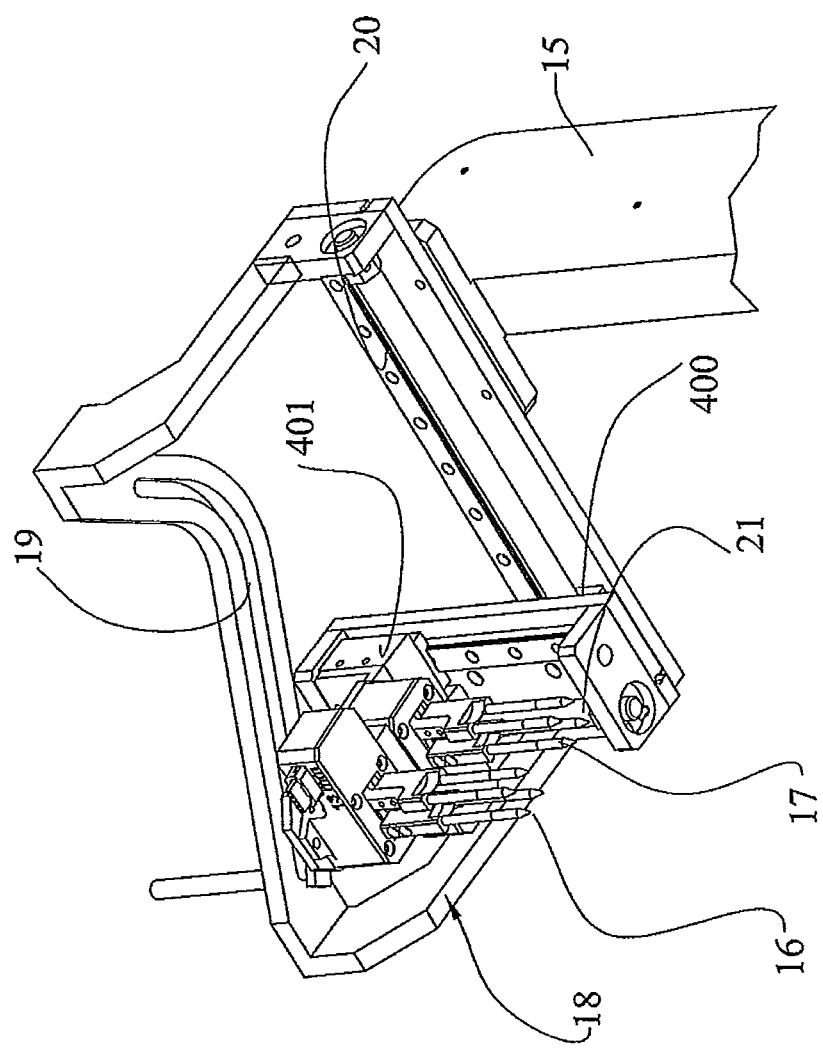
FIG. 5 shows a perspective view of the test tube handling device.

The test tube handling device 8 (FIG. 5), fastened to the centrifuging apparatus 1 by means of a mount 15, comprises an arm 18 with two grippers 16 and 17 capable of gripping and releasing test tubes 3. The reason why two grippers are present derives from the desire of paralleling the loading/unloading operations as much as possible.

When the handling device is above the position 100 on the conveyor 2, there are two operations to be performed (FIG. 2):

releasing a centrifuged test tube in a conveying device 6 stopped at point 105, which operation is performed by the gripper 17;

gripping a test tube to be centrifuged contained in a conveying device 6 at point 106, which operation is performed by the gripper 16.

Points 105 and 106 of position 100 correspond to points 107 and 108 of the centrifuge 9 at position 104.

In brief, we may state that:

gripper 17 operates on points 105 at which the test tubes are unloaded, and at point 108 from which the test tubes are loaded;

gripper 16 operates at points 106 from which the test tubes are loaded, and at point 107 to which the test tubes are unloaded.

Such positions being reversed, the arm 18 sliding on a guide 19 generates a forced rotation of the two grippers due to the followed path, when passing from position 100 to 104 and vice versa. In actual fact, it is a crank-type scheme where an end of the crank is constrained to a path depicted by means of a shaped groove, i.e. guide 19: at the end of the stroke, the two grippers will reverse, thus allowing to reverse the test tubes with respect to the original grip. At each operation of gripping/releasing the test tubes at position 100, the motor 300 is activated so as to allow the centrifuge at position 104 to perform a rotation at an angle such that the cycle may be performed on all twelve yokes of the centrifuge. The pneumatic type movements of the handling device 8 are generated by the shoe 400 sliding on the cylinder 20, for shifting from position 100 to 104, and by the shoe 401 sliding on the cylinder 21, for shifting in the vertical direction.

Figure 6:
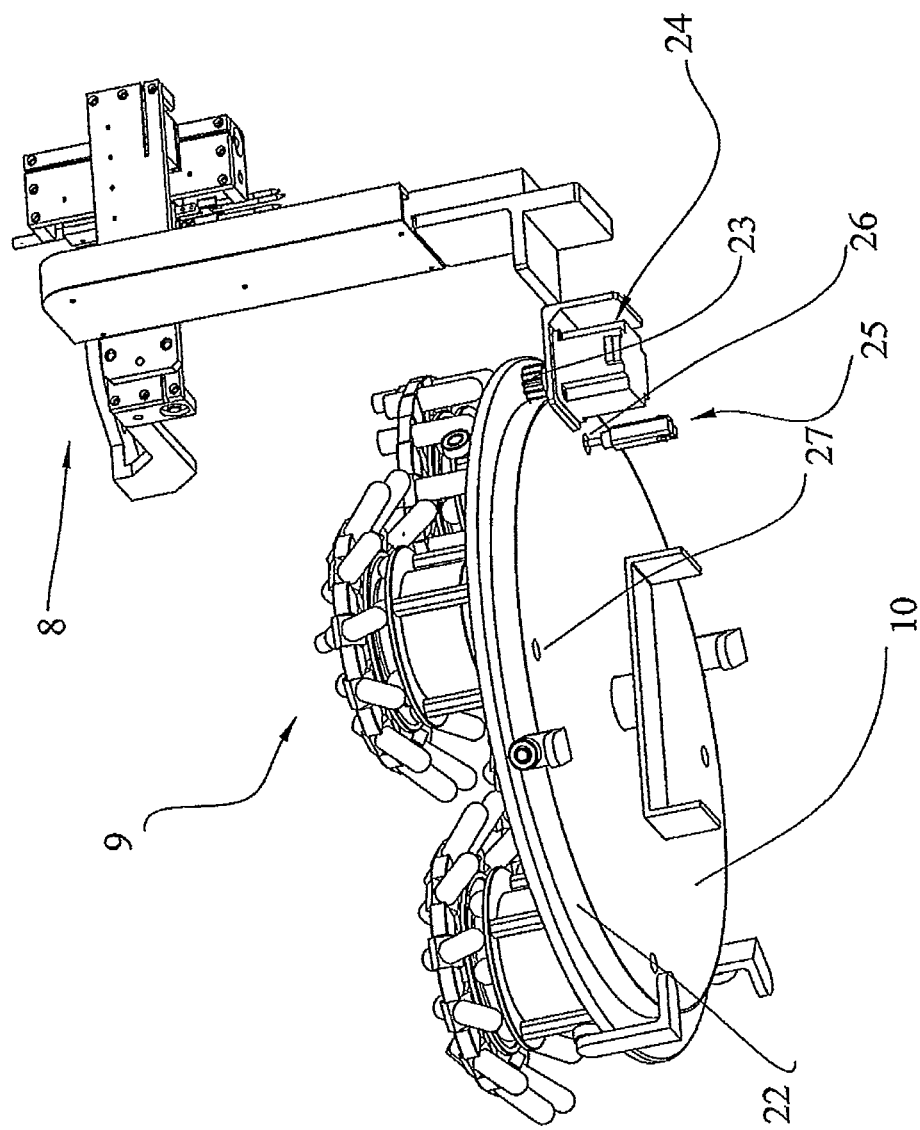
FIG. 6 shows a bottom perspective view of the table of the centrifuges.

Outside the turntable 10, there is a toothed belt 22 (not visible in FIG. 6) with outwardly facing teeth engaging a gear 23 controlled by a motor 24 (FIG. 6).

Said turntable 10 should stop at four, very precise positions in order to allow the centrifuges to be stopped at position 104. Said stops are obtained by means of a pneumatic piston 25 which pulls its movable shaft 26 into and out of four mortises 27.

An embodiment of the invention is described below, which is an alternative to that just set out, but in which the use of centrifuges whose rotors are not able to self-balance is provided, whereby a procedure of balancing the test tubes loaded in the centrifuges is provided.

Figure 7:
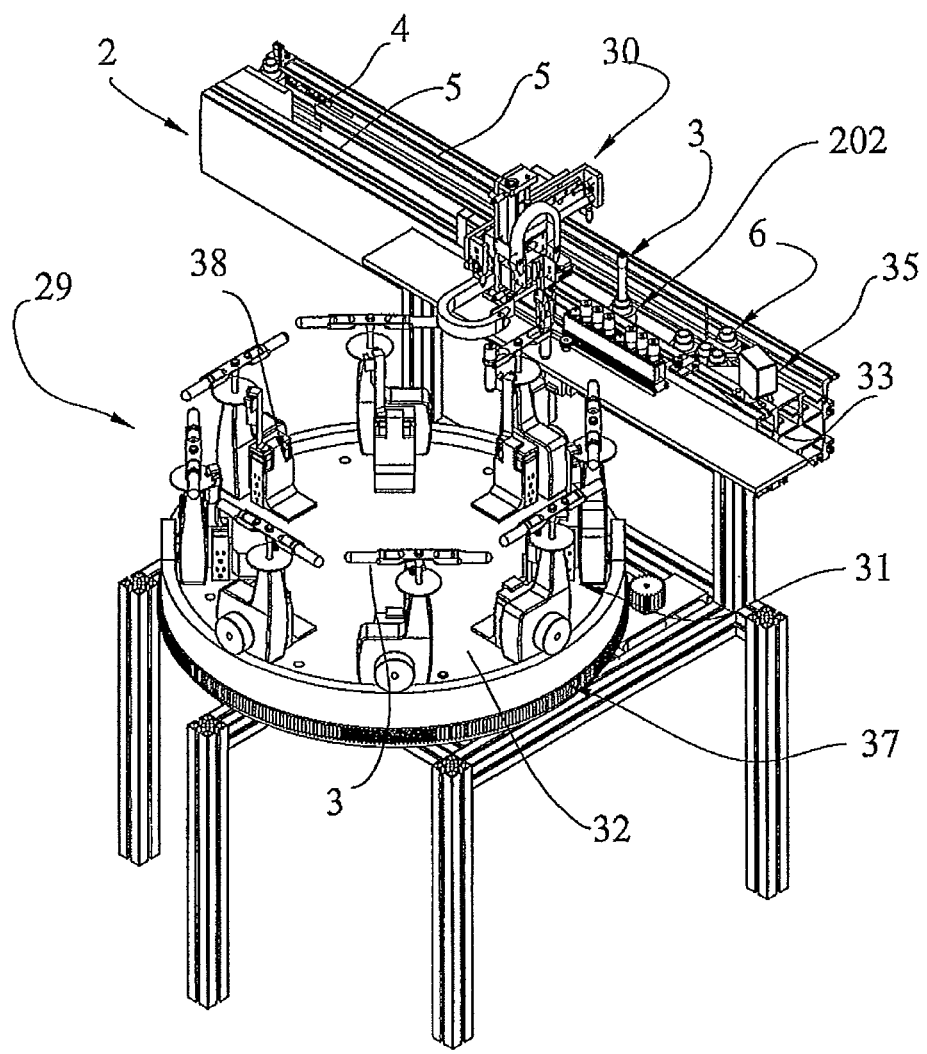
FIG. 7 shows a perspective view of a further embodiment of the apparatus for centrifuging test tubes.

FIG. 7 depicts a centrifuging apparatus 29 fitted on a conveyor 2 completely identical to the one previously described, and adapted to automatically convey test tubes 3 containing biological material samples.

The test tubes 3 conveyed by the conveyor 2 which need to be centrifuged are conveyed into the lane 5 for interfacing with the described apparatus and stopped at a working point 202 adapted to the loading/unloading operations by a handling device 30 (FIG. 7).

The centrifuging apparatus 29 (FIG. 8) comprises a determined number of centrifuges 31 having two locations and adapted to centrifuge as many test tubes per centrifuging cycle.

The number of centrifuges 31 forming the apparatus may vary; the mentioned embodiment comprises eight centrifuges independently operating from one another.

Figure 8:
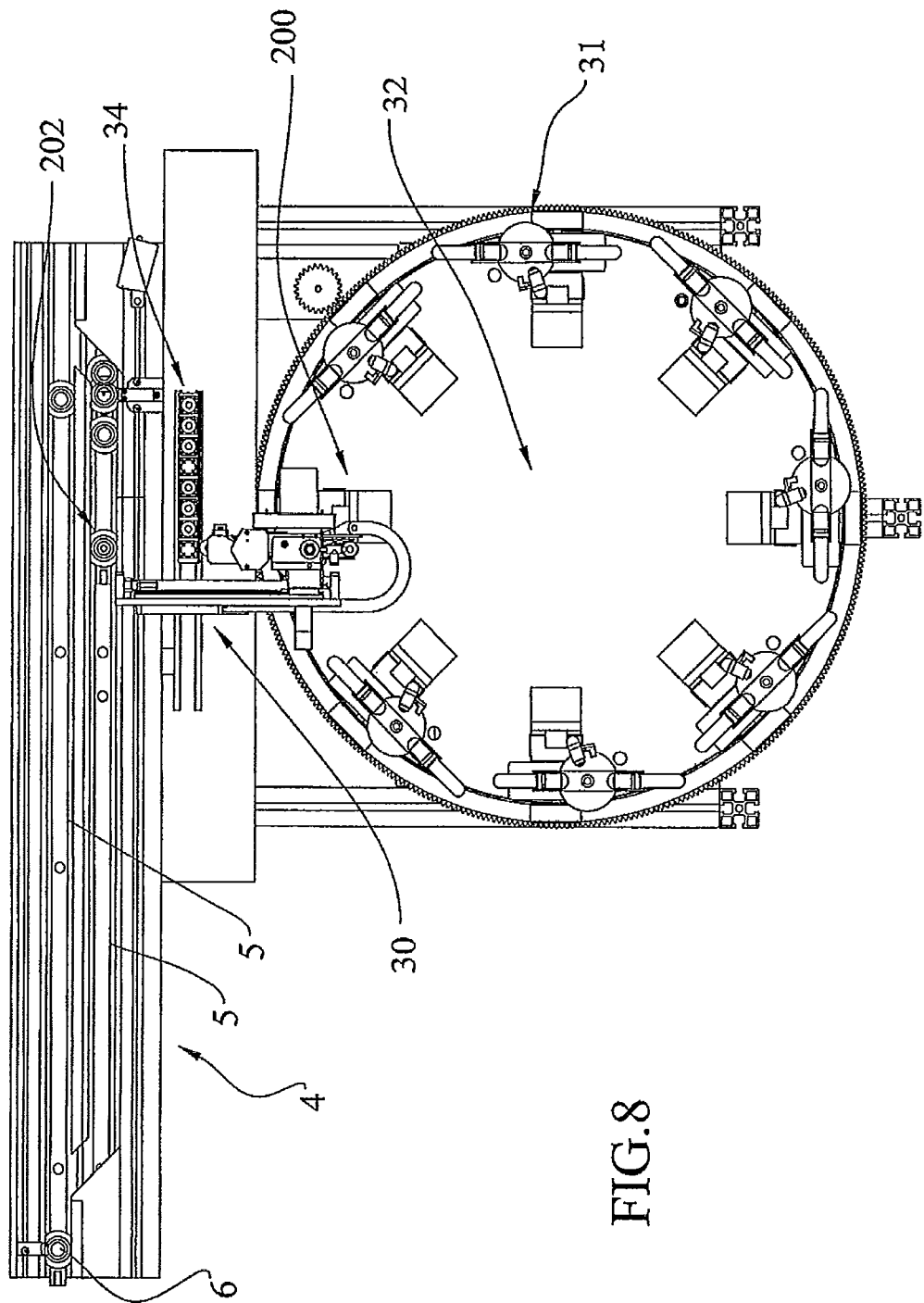
FIG. 8 shows a top plan view of the apparatus for centrifuging test tubes.

The centrifuges 31 are fitted on a turntable 32 serving the function of offering the centrifuges at the loading/unloading point of the test tube, corresponding to position 200 indicated in FIG. 8, which may be accessed by the handling device 30.

In such a position, said test tube handling device 30 may load or unload (at the end of the centrifugation) the test tubes 3 to/from the conveying devices 6 present at working point 202.

Figure 11:
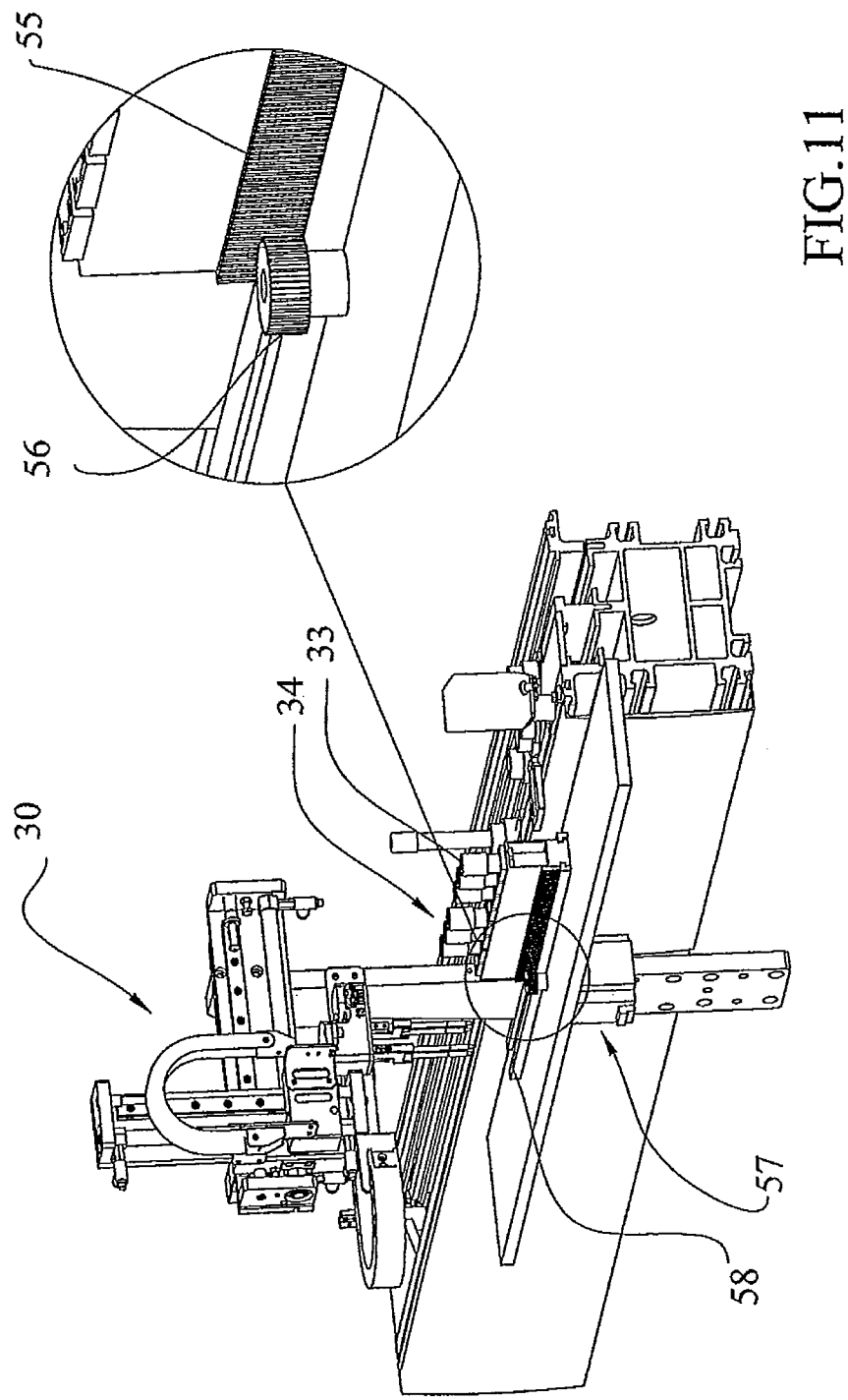
FIG. 11 shows a perspective view of the linear container for the balancing test tubes.

In order to appropriately balance the centrifugal movement of the centrifuges, each centrifuge must be loaded with two test tubes as it is bi-located. In the presence of a single test tube to be centrifuged, the apparatus may employ balancing test tubes 33 (FIGS. 7 and 11) contained into a linear test tube container 34, which may contain up to eight balancing test tubes 33 or however a number equal to the number of centrifuges 31 provided in the apparatus.

According to the explanation, the handling device 30 may be of two types according to the desired performances to be obtained from the described apparatus:

a handling device capable of reaching two locations (one for gripping on the conveyor 2 at working point 202 and one for depositing on the centrifuge 31 and vice versa). In this first solution, the centrifuge 31 is equipped with a single loading position, since one position is permanently occupied by a balancing test tube 33;

a handling device capable of reaching four aligned locations, one of which is on the conveyor 2 at working point 202, two for depositing as many test tubes on the centrifuge 31 and the last one to be able to remove/add a balancing test tube 33 from/to the linear test tube container 34 (as it will be described below).

In this second solution used in the embodiment here described, both locations of the centrifuge 31 may accommodate test tubes 3 to be centrifuged but, in the absence of a pair of test tubes arrived on the conveyor in a short time interval, a balancing test tube 33 which will be picked up from the linear container 34 is required. As it will be later described in detail, the linear container 34 is provided for being able to slide perpendicularly (90°) to the linear course of the handling device 30 (FIG. 11), such that it will make the required balancing test tube available at a location which is aligned with the other 3 reachable locations.

An appropriately loaded centrifuge 31 may initiate the centrifugation, whose length and speed are determined according to the requirements of the analysis laboratory where the operation occurs. While rotating, the turntable 32 arranges an empty centrifuge 31 at position 200, so as to allow the process of loading such a centrifuge 31 in case urgent test tubes are offered at loading point 29, while the previously loaded centrifuge 31 may perform the centrifuging process in another position. At the end of the centrifugation, the turntable 32 places the centrifuge at position 200 again, and the handling device 30 unloads the test tube(s) 3 in conveying devices 6 offered at working point 202, or the balancing test tube 33 (if used) at the origin location of the linear test tube container 34.

Close to the working point 202, the conveyor may comprise test tube identification devices 35 which identify the centrifuged and unloaded test tube by reading its bar code included in the tag arranged on the side body of the test tube, for example.

Each centrifuge 31 is equipped with a rubber treaded wheel 36 (FIG. 10) intended to be coupled with a planetary gear or rotatable crown 37 (FIGS. 7 and 9) adapted to frictionally transmit the motion to all the centrifuges 31 included in the apparatus. Such a planetary gear 37 is thus responsible for the centrifuging process of each centrifuge. In order to obtain the above, each centrifuge 31 is fitted on the turntable 32 by means of a double pneumatic piston 38 fixed on one side to the table 32 and, on the other, by the side of the centrifuge 31 (FIG. 10). Said piston 38 may be driven both downwardly (thus obtaining the control for actuating the motor) and upwardly (thus obtaining an idle position).

The vertical climb is constrained by a mechanical stopper 39 (FIG. 10) which allows the centrifuge 31 to climb again as much as needed in order to de-couple the rubber treaded wheel 36 from the planetary gear 37.

The mechanical coupling between rubber treaded wheel 36 and planetary gear 37 is not instantaneous but it occurs by friction, so that in the starting step there will be a sliding for a few seconds which will gradually diminish up to reach a direct grip. The planetary gear 37 is preferably made of metal, so as to allow the rubber treaded wheel 36 to softly synchronize with the movement of the planetary gear itself by sliding on the metal planetary gear until reaching the synchronization.

The stop of the motion transmission at the end of the centrifuging time occurs by actuating the above-mentioned piston 38, so as to interrupt the forced contact between rubber treaded wheel 36 and planetary gear 37, whereby the motion transmission no longer occurs.

The movements of the planetary gear 37 and turntable 32 are independent from each other.

Each centrifuge 31 (FIG. 10) includes a rotor 40 comprising two movable housings 18 adapted to accommodate as many test tubes. Said housings 18 are fitted on a shaft 210 fitted on the rotor 40 and set in rotation by the rotor itself.

The rotation of the rubber treaded wheel 36, frictionally obtained as previously explained, is transmitted to said rotor 40 which allows the pair of test tubes to be centrifuged due to its rotation.

FIG. 7 depicts the apparatus during the processing of seven centrifuges and the process of loading/unloading one of them, at position 200. The centrifugal force applied to the two movable housings 18 containing test tubes obviously causes a horizontal positioning during the centrifugation of said housings, as depicted in FIG. 7, while the centrifuge is in the configuration of FIG. 10 when in a resting position.

Stopping the rotor 40 of centrifuge 31, which has to undergo the loading/unloading operation, must occur in a specific angular position, so as to allow the loading/unloading operation by the handling device 30 (the correct stop position of rotor 40 is depicted by the centrifuge 31 at position 200 in FIG. 7).

The positioning of rotor 40 in the required angular position may be obtained at the end of the centrifugation by not air-powering the pneumatic piston 30 which, in such an "idle" state, may descend due to the gravity so as the rubber treaded wheel 36 coming in soft contact with the planetary gear 37 may transmit a poor feed to rotor 40, thus allowing the maneuver of correct angular positioning of the rotor itself.

Such a correct angular position of rotor 40 is detected by a system employing an optical sensor 41 (FIG. 10) integrally fitted on the pneumatic piston 38 and adapted to report the presence of a hole 42 existing on the rotor 40, therefore actuating a gripper-type system comprising two ball bearings 43.

Said gripper-type system closes on rotor 40, thus causing the stopping thereof. The lower bearing 43, pneumatically handled by the cylinder 44, closes on the upper bearing 43, by inserting itself into the hole 42 of the rotor 40.

The aim of the signal from the optical sensor 41, appropriately processed by a microcontroller, is to make the gripper-type system formed by the two bearings 43 intervene in order to stop the rotor in the correct position, and possibly measure the angular rotor speed in order to ensure an appropriate centrifuging process.

Figure 9:
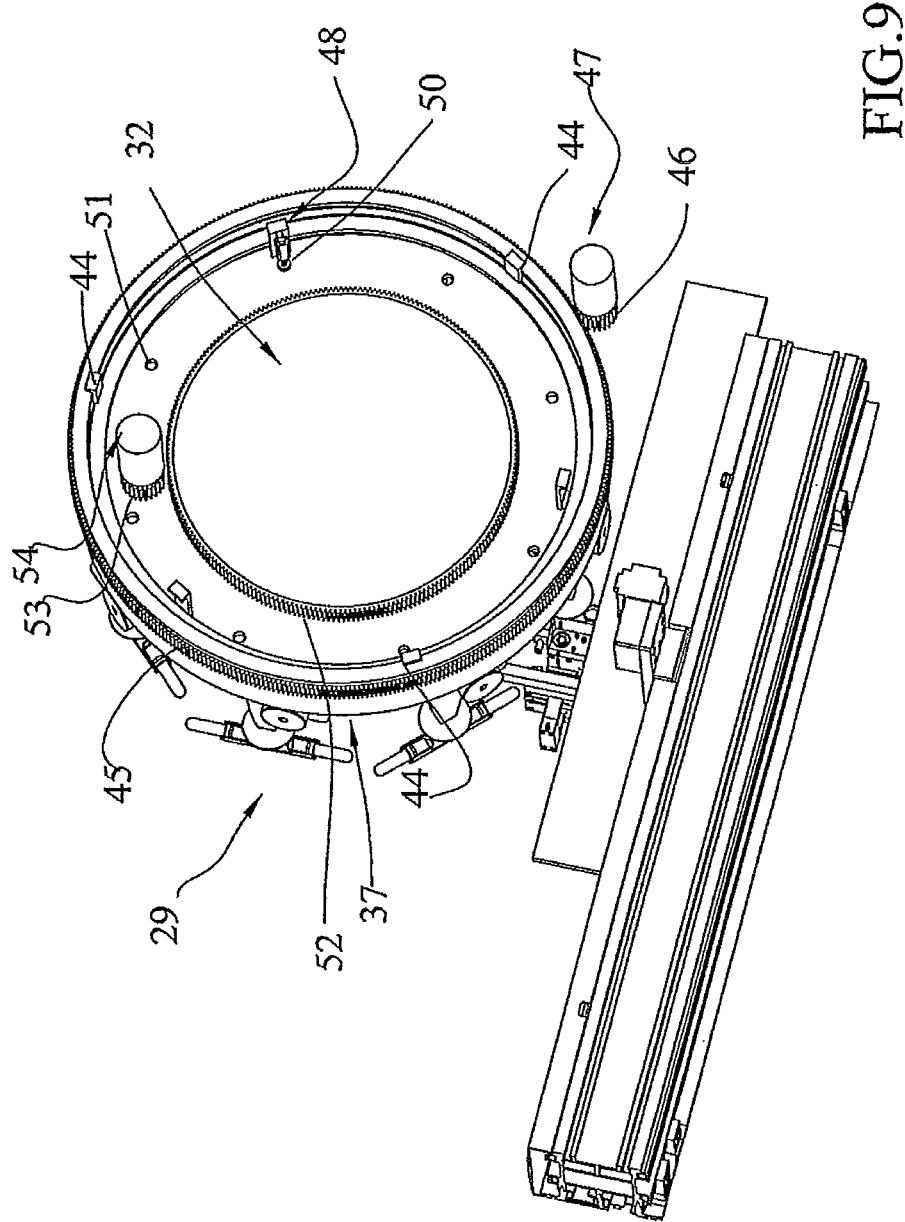
FIG. 9 shows a bottom perspective view of the apparatus for centrifuging test tubes.
Figure 10:
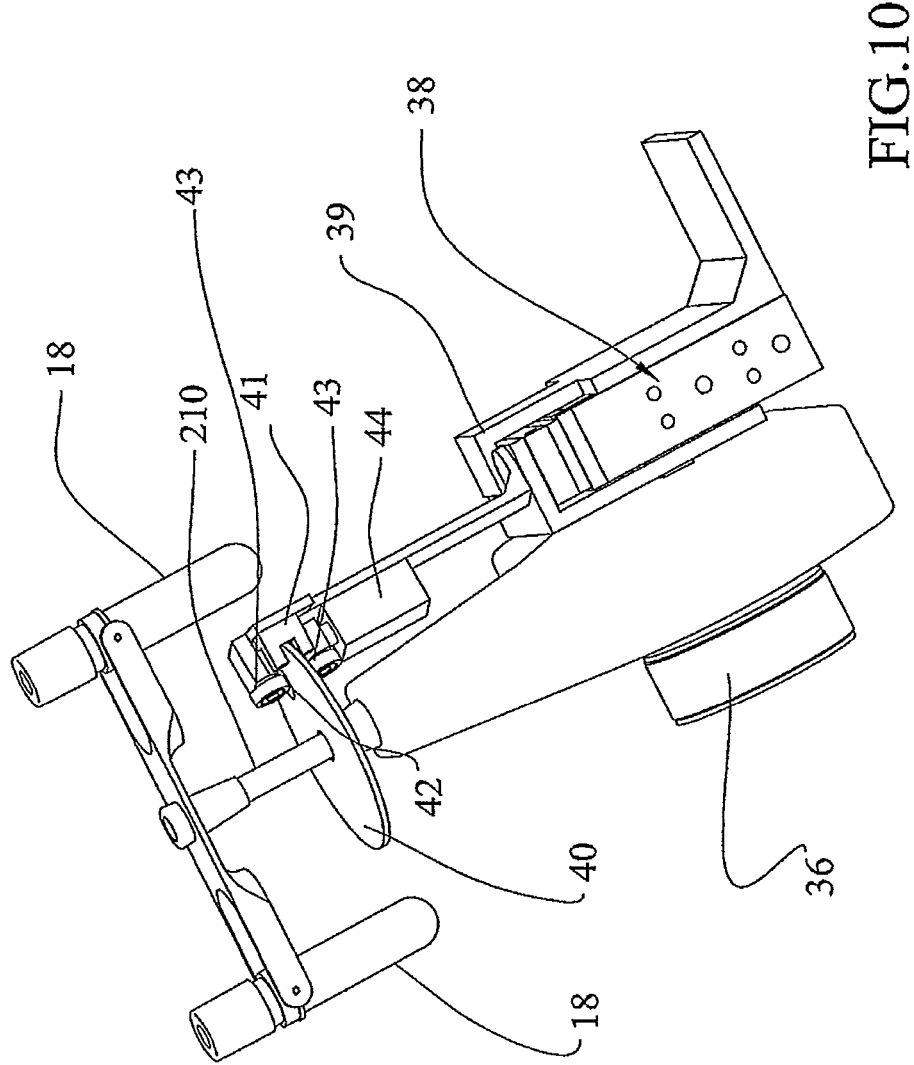
FIG. 10 shows a perspective view of a centrifuge.

The planetary gear 37 consists of a very rigid, circular metal crown; moreover, there is a triplet of bearings 44 arranged at 120° to one another which act both as a horizontal support and a vertical guide (FIG. 9).

Outside the planetary gear 37, there is a toothed belt 45 with outwardly facing teeth which engage a gear 46 controlled by a motor 47.

The turntable 32 is free to rotate about a vertical axis coaxial to the virtual axis of the planetary gear.

Said turntable 32 must stop at eight very precise positions in order to allow the centrifuges to be loaded/unloaded. Said stops are obtained by means of a pneumatic piston 38 which pulls its movable shaft 50 into and out of eight mortises 51, as pointed out in FIG. 3.

Outside the turntable 32, there is a toothed belt 52 with outwardly facing teeth which engage a gear 53 controlled by a motor 54.

The translation of the linear container 34 is obtained by means of an externally fitted rack 55 (FIG. 11) engaged by a gear 56 controlled by a stepping motor 57, whose movement generates the translation of the linear container 34 inside the guides 58.

The invention claimed is:

1. An apparatus for automatically centrifuging test tubes containing biological material, comprising:
    a plurality of centrifuges functionally identical to one another yet independent and adapted to centrifuge test tubes offered to an interface for centrifuging test tubes by means of a conveying system included in an automatic conveyor of test tubes, the plurality of centrifuges rotatably mounted on a turntable adapted to offer each centrifuge at a suitable loading/unloading position adjacent to the loading/unloading point of the interface, wherein each centrifuge is provided with a motor adapted to generate the centrifugal motion by setting a rotor in rotation; and
    a test tube handling device comprising an arm with a first gripper adapted to load test tubes to be centrifuged and a second gripper adapted to unload centrifuged test tubes, simultaneously to said loading, said arm sliding along a curved guide adapted to generate a forced rotation of the grippers.

2. The apparatus according to claim 1, further comprising a stop piston engaging with mortises placed at each centrifuge, in order to block the turntable such that each centrifuge is matched in the loading/unloading position.

3. An apparatus for automatically centrifuging test tubes containing biological material, comprising a plurality of centrifuges functionally identical to one another yet independent and adapted to centrifuge test tubes offered to an interface for centrifuging test tubes by means of a conveying system included in an automatic conveyor of test tubes, the plurality of centrifuges rotatably mounted on a turntable adapted to offer each centrifuge at a suitable loading/unloading position adjacent to the loading/unloading point of the interface,
    wherein the turntable is rotatably coaxial and independent with respect to a centrifuging crown which may rotate at a predetermined speed and adapted to be coupled with wheels for controlling the centrifuges.

4. The apparatus according to claim 3, wherein each centrifuge comprises a pneumatic piston adapted to control the vertical motion of the wheel of the centrifuges between an idle position and a position of friction with the moving centrifuging crown.

5. The apparatus according to claim 4, wherein each centrifuge comprises an optical sensor adapted to report the presence of a hole on a rotor, on which two movable housings adapted to accommodate as many test tubes are fitted, in order to actuate gripper means adapted to block the rotor in a position such that said movable housings are aligned with the loading/unloading point of the interface.

6. The apparatus according to claim 5, further comprising a translatable container of balancing test tubes to be loaded in one of the housings of the centrifuge in the case of a single test tube to be centrifuged.

7. The apparatus according to claim 5, further comprising a stop piston engaging with mortises placed at each centrifuge, in order to block the turntable such that each centrifuge is matched in the loading/unloading position.

8. The apparatus according to claim 4, further comprising a translatable container of balancing test tubes to be loaded in one of housings of the centrifuge in the case of a single test tube to be centrifuged.

9. The apparatus according to claim 4, further comprising a stop piston engaging with mortises placed at each centrifuge, in order to block the turntable such that each centrifuge is matched in the loading/unloading position.

10. The apparatus according to claim 3, further comprising a translatable container of balancing test tubes to be loaded in one of two moveable housings of the centrifuge in the case of a single test tube to be centrifuged.

11. The apparatus according to claim 10, wherein the location of the translatable container involved in the process of loading/unloading the balancing test tube is placed in alignment with the two housings of the centrifuge and with the loading/unloading point of the interface.

12. The apparatus according to claim 11, further comprising a stop piston engaging with mortises placed at each centrifuge, in order to block the turntable such that each centrifuge is matched in the loading/unloading position.

13. The apparatus according to claim 10, further comprising a stop piston engaging with mortises placed at each centrifuge, in order to block the turntable such that each centrifuge is matched in the loading/unloading position.

14. The apparatus according to claim 3, further comprising a stop piston engaging with mortises placed at each centrifuge, in order to block the turntable such that each centrifuge is matched in the loading/unloading position.

* * * * *